United States Patent
Ko

(10) Patent No.: US 11,298,055 B2
(45) Date of Patent: Apr. 12, 2022

(54) IN VIVO, NONINVASIVE, BIOELECTROMAGNETIC GLUCOSE SENSOR SYSTEM AND METHOD

(71) Applicant: Harvey W. Ko, Ellicott City, MD (US)

(72) Inventor: Harvey W. Ko, Ellicott City, MD (US)

(*) Notice: Subject to any disclaimer, the term of this patent is extended or adjusted under 35 U.S.C. 154(b) by 0 days.

(21) Appl. No.: 17/305,787

(22) Filed: Jul. 14, 2021

(65) Prior Publication Data
US 2022/0015669 A1    Jan. 20, 2022

Related U.S. Application Data

(60) Provisional application No. 62/705,741, filed on Jul. 14, 2020.

(51) Int. Cl.
  *A61B 5/145* (2006.01)
  *A61B 5/01* (2006.01)
  *A61B 5/00* (2006.01)

(52) U.S. Cl.
  CPC .......... *A61B 5/14532* (2013.01); *A61B 5/01* (2013.01); *A61B 5/14535* (2013.01); *A61B 5/14542* (2013.01); *A61B 5/6826* (2013.01); *A61B 5/6838* (2013.01); *A61B 5/7203* (2013.01); *A61B 5/742* (2013.01)

(58) Field of Classification Search
  None
  See application file for complete search history.

(56) References Cited

U.S. PATENT DOCUMENTS

| 4,690,149 | A | * | 9/1987 | Ko | ........ | A61B 5/0507 |
| | | | | | | 600/409 |
| 2002/0095075 | A1 | * | 7/2002 | Madarasz | ............ | G01N 21/21 |
| | | | | | | 600/310 |
| 2010/0026995 | A1 | | 2/2010 | Merritt et al. | | |
| 2017/0231536 | A1 | * | 8/2017 | Bharj | .............. | A61B 5/0507 |
| | | | | | | 600/316 |
| 2020/0345280 | A1 | * | 11/2020 | AlShawoosh | .......... | G01R 33/20 |

OTHER PUBLICATIONS

International Search Report and Written Opinion; PCT/US2021/071286; dated Sep. 29, 2021.

* cited by examiner

*Primary Examiner* — Marjan Fardanesh
(74) *Attorney, Agent, or Firm* — Dunlap Bennett & Ludwig, PLLC; Anna L. Kinney

(57) ABSTRACT

A noninvasive glucose monitoring device includes a drive-and-sense coil and an electronic oscillator with multiple circuits electrically connected to the coil. The drive-and-sense coil may be embedded in either a finger clip or a finger push button. The device measures bioimpedance with a magnetic field coil outside a user's finger. The coil measures blood and glucose electrical conductivity without penetrating the finger. No blood extraction is required. A noninvasive method of measuring glucose in-vivo includes placing the drive-and-sense coil next to a subject's finger and inducing magnetic fields in blood in the subject's finger. A change in mutual impedance between the drive-and-sense coil and the blood is measured at predetermined frequencies and glucose content is calculated from the change in mutual impedance according to a predetermined correlation for each frequency.

12 Claims, 5 Drawing Sheets

IN VIVO, NONINVASIVE, BIOELECTROMAGNETIC GLUCOSE SENSOR SYSTEM AND METHOD

CROSS-REFERENCE TO RELATED APPLICATION

This application claims the benefit of priority of U.S. provisional application No. 62/705,741, filed Jul. 14, 2020, the contents of which are herein incorporated by reference.

BACKGROUND OF THE INVENTION

The present invention relates to devices for monitoring blood glucose levels and, more particularly, to a noninvasive bioelectromagnetic sensor for monitoring glucose in vivo.

Worldwide, millions of people, especially diabetics, need to monitor their blood glucose level frequently every day. Existing at-home devices require skin pricks to emanate blood. The skin prick method requires 5 steps with 2 devices: swabbing the prick area with alcohol wipes, loading a fresh glucose strip into the glucose monitor device, arming the lancet prick lancing device with a prick needle, pricking the finger to exude blood, placing the glucose strip properly into the blood pool, and observation of the readout of glucose level in milligrams per deciliter (mg/dL). The replenishment of needles/lancets and electrode/enzyme test strips with limited shelf life is expensive with components linked to each manufacturer's monitor (i.e., they are not universal). The skin prick is a nuisance, painful, and can be frightening.

The enzyme/needle-stick systems give large errors if used beyond their shelf life and their replenishment is complicated. Furthermore, glucose values taken from two successive blood strips of the same blood spot can give glucose values as much as 20% different from each other.

Implantable, continuous systems require a clinically trained professional for electrode insertion and diagnostics (often via a fickle internet) and need to be replanted after each week or so. These implantable devices measure changes in interstitial fluid and not blood alone. Also, they cannot be exposed to excess moisture (e.g., rain, bathing). Other electromagnetic (EM) systems rely on small skin depth penetrating wavelengths (near infrared, optical) using very expensive laboratory grade equipment. See Bera, T. K., "Bioelectrical impedance methods for noninvasive health monitoring; a review", Journ Medical Eng., 2014; Vashist, S. K., "Non-invasive glucose monitoring technology in diabetes management", Analytica Chimica Acta, 750, 2012; and Zhang, R., et al, "Noninvasive electromagnetic wave sensing of glucose" 2016 preprint, the disclosures of which are incorporated herein by reference.

EM small wavelength systems, used primarily in research on animals, have errors due to EM absorption by substances other than glucose and the motility and electrical permittivity differences between erythrocytes. EM spectroscopy methods used in research are dominated by skin electrical potential which is difficult to discern from blood voltages. EM spectroscopy methods require expensive laboratory equipment and are not suitable for home use. Many investigators give conflicting values, mostly for animal blood, and the measurements by skin electrodes are not relevant to an inner volume method. See Schwan, H. P. "Electrical properties of blood and its constituents; alternating current spectroscopy", Blut, 46, 1983; Wolf, M., et al, "Broadband Dielectric Spectroscopy on human blood", phys bio preprint, March 2015; Caduff, A., et al., "Continuous noninvasive glucose monitoring: water as a relevant marker of glucose uptake in vivo", Biophys Rev, 11, 2019; Talary, M. S., et al, "Non-invasive impedance based continuous glucose monitoring system", IFBME Proc 17, 2007; Juansah, J., et al., "Studies on electrical behavior of glucose using impedance spectroscopy", IOP Conf Ser: Earth Environ. Sci., 31, 2016; Abdalla, S., et al., "Electrical properties with relaxation through human blood", BioFluidMech, 4, 2010; Desouky, O. S., "Rheological and electrical behavior of erythrocytes in patients with diabetes mellitus", Romanian Biophys, 19, 2009; and Weinart, R. L., et al, "Detection of glucose by using impedance spectroscopy", ICBCI 16th international conf electrical bioimpedance, 2016, the disclosures of which are incorporated herein by reference.

As can be seen, there is a need for a sanitary, noninvasive method of monitoring blood glucose levels in vivo, without blood pricks, and without multiple expensive, expendable components.

SUMMARY OF THE INVENTION

In one aspect of the present invention, a noninvasive glucose monitoring system is provided, comprising: a finger clip having a drive-and-sense coil operative to measure blood and glucose electrical conductivity without penetrating the finger; and an electronic oscillator with a plurality of circuits in electrical communication with the finger clip. The system is operative to measure bioimpedance with magnetic field coils outside a user's finger.

In another aspect of the present invention, a noninvasive method of measuring glucose in-vivo is provided, comprising: placing a drive-and-sense coil adjacent to a subject's finger or pressing the subject's finger against a drive-and-sense-coil button; inducing magnetic fields in blood in the subject's finger; measuring a change in mutual impedance between the drive-and-sense coil and the blood at a predetermined frequency; and calculating a glucose content from the change in mutual impedance according to a predetermined correlation.

These and other features, aspects and advantages of the present invention will become better understood with reference to the following drawings, description, and claims.

DETAILED DESCRIPTION OF THE INVENTION

Figure 1:
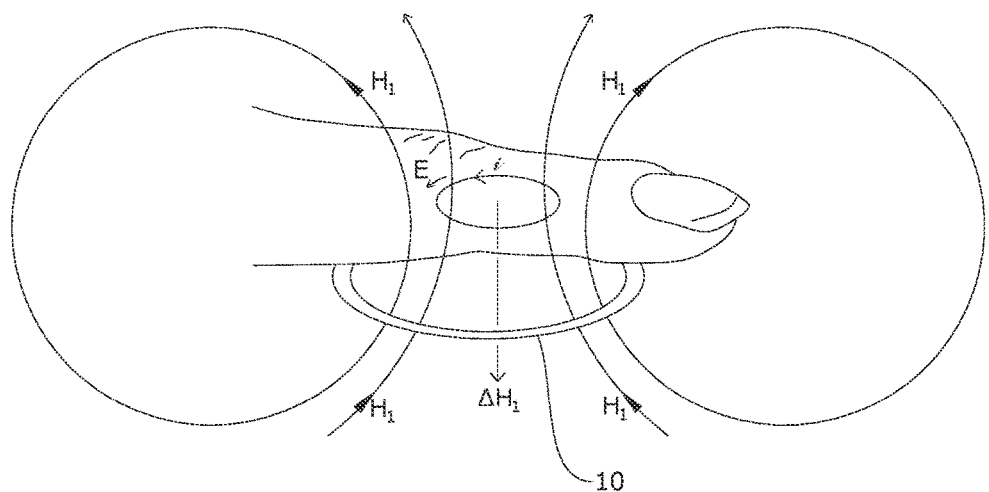
FIG. 1 is a schematic view of the physical principles of a method of sensing glucose electrical impedance according to an embodiment of the present invention.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is an easy to use, noninvasive glucose monitoring system. The system is operative to measure bioimpedance (i.e., bioelectrical impedance) with magnetic field coils outside the finger, not electric field electrodes either on or under the skin. The system is totally noninvasive since it does not require a skin prick to emanate blood or clinical implantation of a device under the user's skin. The system is completely portable, battery operated, and may be used in personal venues, with no expendable replacement parts like prick needles and enzyme electrode test strips.

With over 200 trials, using the prior art blood prick monitors for reference values of glucose level in mg/dL, this invention has shown the efficacy of a single, sanitary device and method, without drawing blood, of determining blood glucose values, especially in the diabetic range of 100 to 175 mg/dL. In addition, the inventor has shown the value of a multiple frequency measurement approach that increases the statistical degrees of freedom for greater accuracy.

The present invention provides a sensor system which uses electromagnetic induction to measure blood and glucose electrical conductivity with a non-skin-penetrating drive coil. The coil may be placed next to a finger to measure the change in mutual impedance between the drive coil and the magnetic fields induced by electrical currents in the finger blood volume, which are in turn induced by the drive coil. This electromagnetic induction method and a simple (i.e., single predetermined frequency) version of a sensor module has been used successfully for the noninvasive detection of brain edema, prostate tumor, and osteoporosis. The present invention exploits the multi-frequency characteristics of blood and glucose. See Ko, H. W., et al., "The APL Bioelectromagnetics Laboratory", Johns Hopkins APL Tech Dig. 7, 1986, pp. 300-307; Hart, L. W., et al., "A noninvasive electromagnetic conductivity sensor for biomedical applications", IEEE Trans Biomed, 35, 1988; Smith, D., et al., "InVivo measurement of tumor conductivities with the bioimpedance method", IEEE Trans Biomed, 47, 2000; Long, D. M., et al., "Quantification of brain edema by measurement of brain conductivity", Springer Verlag Brain Edema, 1985; Schwan, supra; Wolf, supra; Abdalla, supra; and Desouky, supra; and U.S. Pat. Nos. 7,283,868, 4,860,756, 4,850,372, 4,819,648, 4,690,149, and 4,688,580, the disclosures of which are incorporated herein by reference.

The present invention also provides a safe, more comfortable, continuous glucose monitoring method as compared to currently commercially available tests and may replace the hundreds of thousands of home use finger-pricking glucose systems sold today. The inventive method has been shown to measure blood glucose without the need for a skin prick or implantable device. The inventive device is completely self-contained, reusable, portable, does not require expendable components except for batteries, and may be used without the need for a healthcare professional.

The system may be operated either by placing a small coil clip onto a user's finger (just like a pulse oximeter) or by having the subject's finger push a button that contains the drive-sense coil. The patents and the articles to Ko, Hart, Smith, and Long, supra, explain the principles of operation of the singular drive-sense coil used in the inventive system.

The inventive single finger drive coil may operate at various frequencies. Specific radio frequency (RF) choke values and resonant tank capacitances may be associated with published glucose changes prior to use, providing a predetermined correlation between bioimpedance and glucose content.

In some embodiments, the inventive system may include a Colpitts oscillator. Other electronic oscillator designs may also be used.

In some embodiments, electronic miniaturization may be achieved using microcircuitry, including a microprocessor and microcontroller.

In some embodiments, the monitoring system may include an RF noise reduction component and/or an oscillator stability component. Other features may also be included.

In some embodiments, a pulse-oximeter and/or a thermistor may be added. A pulse oximeter sensor may be added based on a predetermined effect of hematocrit on glucose. The addition of each component may increase the degrees of freedom in measurements, giving rise to more accurate results. See Jaspard, F., et al., "Dielectric properties of blood; an investigation of hematocrit dependence", Inst Phys. Physical Meas., 24, 2003; Beving, H., et al, "Dielectric properties of human blood and erythrocytes at radio frequencies; dependence on cell volume and medium composition", Eur Biophys., 23, 1994; and Teodorczyk, M., et al., "Hemacrit compensation in Electrochemical Blood glucose Monitoring Systems", Journ Diabetes S & T, 6, 2012, the disclosures of which are incorporated herein by reference.

In some embodiments, a display module may be provided to indicate when radiofrequency background values have been determined by the microprocessor and microcontroller functions, at which time the user may insert his or her finger. The display module may show values such as glucose level in mg/dl, Glucose (G) value, and % hematocrit (HcT) value, as well as indicator lights.

A method of using the inventive system may include the following steps. After the system is turned on, the subject waits, while a yellow ("wait") LED indicator light is illuminated, for the microcontroller to cycle through the choke/capacitor elements to obtain RF background data, measured by the drive-sense coil at each oscillator resonant frequency without the subject's finger. After a few seconds, the microprocessor stores the obtained background data and signals the subject, e.g., with a green "wait" LED, a yellow "proceed" LED, and a yellow "memory" LED, to either insert his/her finger into the coil clip or push the coil button. Once the measurements at each frequency are complete (which may take a few seconds), the microprocessor calculates the G value in mg/dl at each frequency and calculates an average G value. The microprocessor stores the date, time, and average G value in memory and signals that the measurement is complete by displaying all green LEDs. The final G value average is shown on the digital, numeric display, along with a % HcT value if a pulse oximeter is used.

The inventive multiple frequency EM bioimpedance sensor may be modified for use detecting brain edema, osteoporosis, prostate cancer, and breast cancer. See Smith and Long, supra.

A system according to an embodiment of the invention may be operated as follows. When the system is switched ON, a microprocessor may command the ON light to be yellow, notifying the user to WAIT a few seconds. The microprocessor-controller may quickly cycle through a series of frequencies to measure the RF background (without finger). The selectable radio frequency (RF) choke and associated resonant tank capacitance defines a different RF Colpitts oscillator circuit as each frequency is selected by a microcontroller. Once the background values have been stored in a data storage module, the microprocessor may change the ON/wait light to green, notifying the user to insert a finger into the coil clip in electrical communication with the Colpitts oscillator and its microprocessor. Once the finger has been inserted, the microprocessor-controller may cycle through each frequency and circuit again, recording glucose impedance measurements. While not limiting the invention, background plus glucose measurements may take about 5 seconds for each frequency. At each frequency, the microprocessor may calculate the voltage output difference between the RF background ($V_0$) and the impedance values attributable to glucose content ($V_2$) at each frequency, the result of which is generally proportional to the amount of glucose present. The microprocessor may consolidate the data to report a single "average" glucose value, mg/dl, on a display. The glucose value associated with each voltage output difference may be preset during factory calibration, using an empirical glucose conductivity value determined by preferably hundreds of empirical glucose values obtained simultaneously by the inventive method and the enzyme strip method with multiple volunteers, such as over a dozen. The glucose value may be derived from the magnetic field and calculated as the fractional voltage change due to the glucose blood measurement, i.e., $deltaV/V_0$=[background voltage value $V_0$]−[voltage with finger in sensor $V_2$]/[background voltage value $V_0$]. The physical theory and circuit principles used herein have been disclosed in Ko, Hart, Smith, and Long, supra.

A basic sensor electronics module allows a single drive-and-sense coil to be operated at EM resonance for n different frequencies in the radiofrequency range from a few kilohertz up to several megahertz. This is accomplished using selectable RF chokes and capacitors. The electrical conductivity is represented by the sensor voltage output according to Ohm's Law, i.e., voltage V=current I×resistance R.

Results of in vitro animal research by Abdalla for the dependence of blood glucose at RF illustrate the different conductivity to frequency curves associated with normal blood and diabetic blood that the invention exploits. See Schwan, supra; Wolf, supra; Abdalla, supra; and Desouky, supra; see also FIG. 5. At each frequency, the microprocessor may calculate the difference between the background and the glucose values, the difference being proportional to the impedance/glucose value. However, an embedded, submerged electrode is not required. In any case, the glucose values may be independently determined at a plurality of frequencies, thereby increasing the degrees of freedom in the measurements, and giving rise to more accurate results.

A system according to an embodiment of the invention has been proven to be noninvasive, small, battery-safe operationally, with no expendables (other than batteries). The glucose fractional voltage change from the background level is $[V_0-V_2]/V_0$ (i.e., $-\Delta V/V_0$). A microprocessor review of all data provides the glucose value given on the display.

Individual data points provide a "baseline" showing the glucose values obtained using a blood lancet/electrode strip commercial measurement device. The blood lancet/electrode strip G data are considered the same for each frequency. However, the immediate succession use of test strips on the same blood spot can give values 30% apart. They demonstrate the variability of the commercial method. Any change in the electronic circuitry will give a different baseline. Therefore, commercial practices that standardize on electronic component tolerance, leakage capacitance, and other fabrication changes are advantageous. For each sensor electronic embodiment different baselines are determined at multiple oscillator resonant frequencies, each frequency determined by the choke-capacitor, sense coil, and tank circuit.

The "baseline" is the value of $-\Delta V/V_0$ of actual tests with volunteers who have a variety of diabetes G values. As different people are measured with the same electronic circuitry, baseline charts are used to determine their G value. FIG. 6 is an example of baseline G charts for the frequencies of 7, 5, 3, and 0.3 MHz.

Data was collected from 8 volunteers. The hematocrit levels measured amongst the 8 volunteers showed little or no effect on the sensors used herein. Volunteers also operated the devices to change oscillator frequencies and to calculate glucose values by computer algorithms.

Referring to FIGS. 1 through 6D, FIG. 1 illustrates the physical principles of a method of sensing the glucose electrical impedance in a subject's finger according to an embodiment of the present invention. In FIG. 1, a drive-and-sense coil 10 is placed under a finger. E is the magnitude of the electric field, $H_1$ indicates the impressed field and $\Delta H_2$ indicates the magnetic field calculated as the difference between the impressed field $H_1$ and the induced field $H_2$ in accordance with Lenz's Law that states that the field direction of the induced magnetic field is directionally opposite from the direction of the driving field. Therefore, the accompanying voltage changes are the algebraic difference between the drive and sense voltages, also opposite in polarity. The magnetic field, $\Delta H_2$, is generally proportional to the conductivity of the blood media that contains the glucose (see FIG. 5). The voltage $V_2$ discussed above is generally proportional to $\Delta H_2$. See Abdalla, supra. The time constants and variations are given by the inverse of each frequency.

Figure 2:
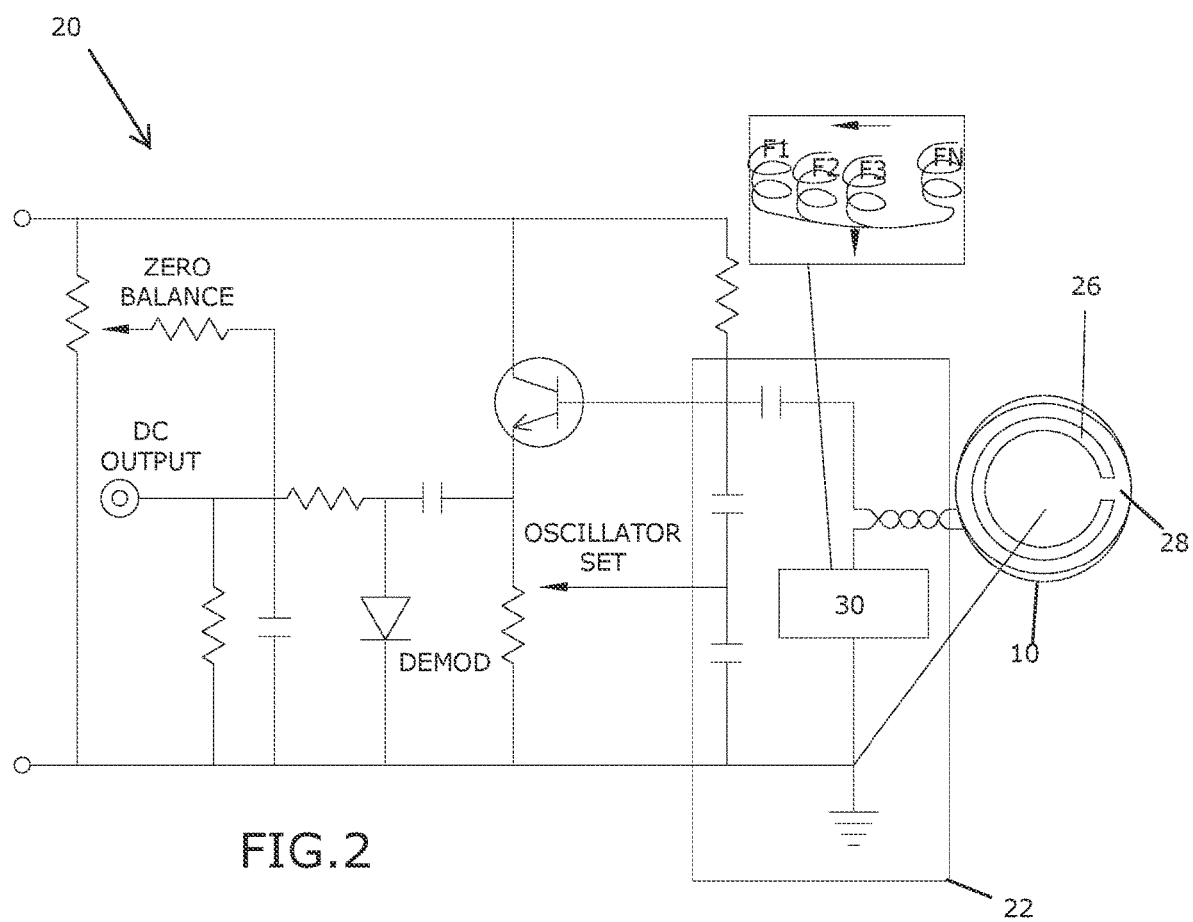
FIG. 2 is a schematic view of a Colpitts oscillator sensor module according to an embodiment of the present invention.

FIG. 2 illustrates a Colpitts oscillator sensor module 20 according to an embodiment of the present invention. A coil 10 having a copper strip shield 26 with a gap 28 and a tank circuit 22 with an RF choke bank 30 (a series of N inductors F that suppress high frequency alternating circuit signals) outputs signal moderated by capacitors to an oscillator set. The module is also equipped with a zero balance circuit and a demodulator and emits a direct current (DC) output signal.

The coil and copper strip shield with gap is a Faraday shield that sends extraneous stray background signals (i.e., noise) to ground. "Oscillator set" refers to set point. At each frequency choke-capacitance combo, the set point sets the behavior of the oscillator at peak resonance for better signal to noise (S/N) ratio. The DC output is delivered to the microprocessor which calculates G value in mg/DL.

Figure 3:
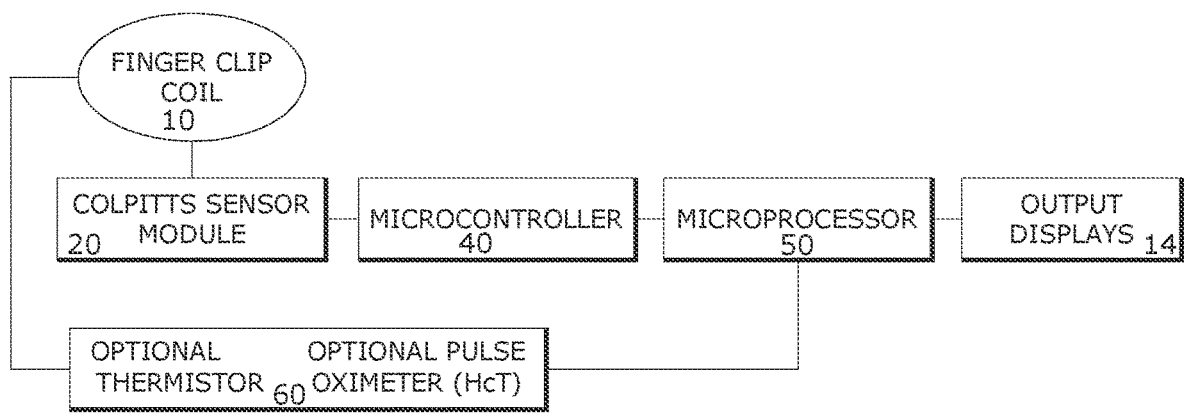
FIG. 3 is a schematic view of the major subsystem elements of a non-invasive glucose measurement system according to an embodiment of the present invention.

FIG. 3 shows the major subsystem elements of a non-invasive glucose measurement system according to one embodiment of the present invention. A finger clip coil 10 feeds data to a Colpitts sensor module 20 which operates with a microcontroller 40 and a microprocessor 50. The microcontroller selects each radiofrequency/Colpitts frequency. The microprocessor calculates the glucose value at each frequency measured. In some embodiments, additional criteria may be measured with additional components 60, e.g., a thermistor to measure temperature, a pulse oximeter to determine oxygen saturation level, dependent upon hematocrit (HcT), or both are linked to the finger clip coil 10 and the microprocessor 50. The microprocessor 50 outputs data to a visual display 14.

Figure 4:
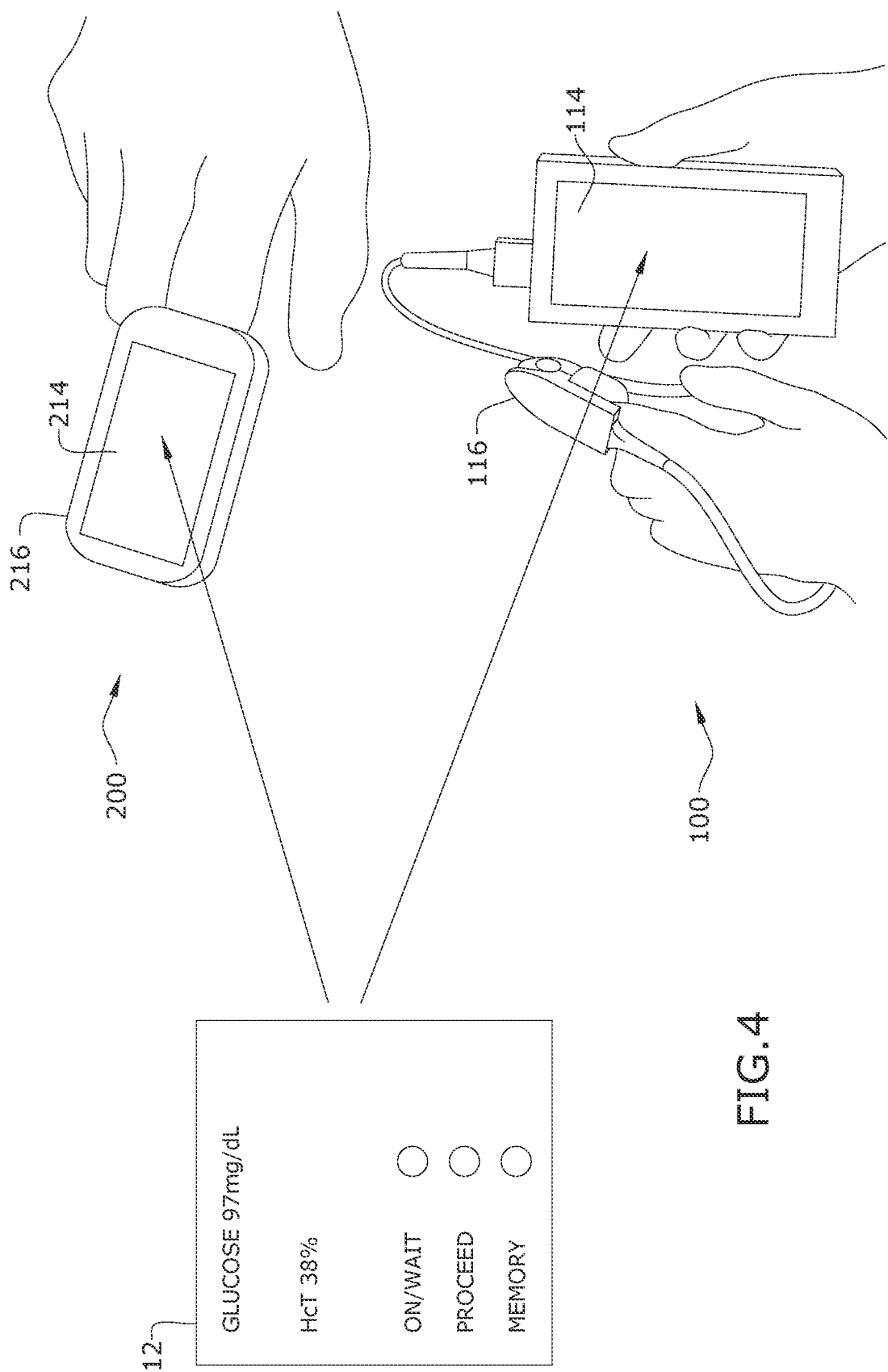
FIG. 4 is a schematic view of additional embodiments of the present invention.

FIG. 4 illustrates two sensor units 100, 200 showing different embodiments of the inventive system. Both units 100, 200 include a finger clip 116, 216 and a display 114, 214. The display may provide information 12 such as the glucose level, the HcT level, and operational information such as whether the unit is on, whether the user should wait or proceed to use the unit, and time history/trends of the patient's glucose history, which aids in monitoring diabetes.

Figure 5:
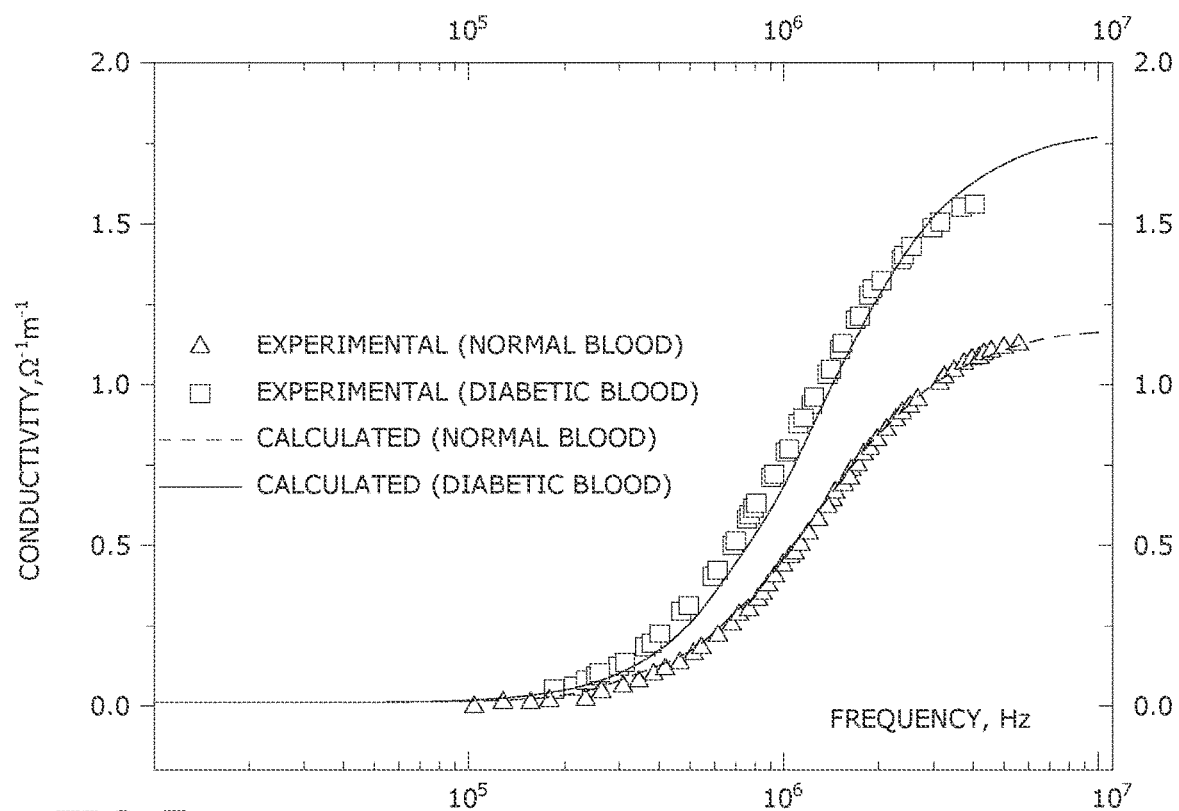
FIG. 5 is a chart of diabetic and normal blood conductivities measured in-vitro with embedded submerged electrodes.

FIG. 5 is a chart showing diabetic and normal blood conductivities measured in-vitro with embedded submerged electrodes as disclosed in Abdalla, supra. Conductivity values in $\Omega^{-1}$ $m^{-1}$ were calculated and measured for a plurality of frequencies in Hz for both blood of a diabetic subject and blood of a non-diabetic subject.

Figure 6A:
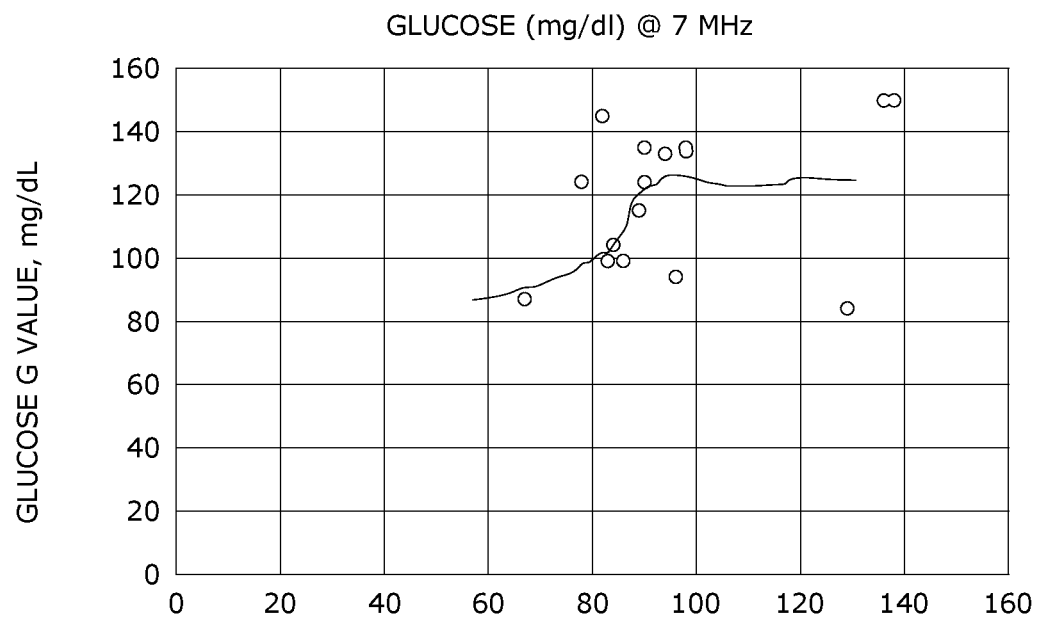
FIG. 6A is a graph of human glucose measured in-vivo by the sensor module of FIG. 2 at 7 MHz.
Figure 6B:
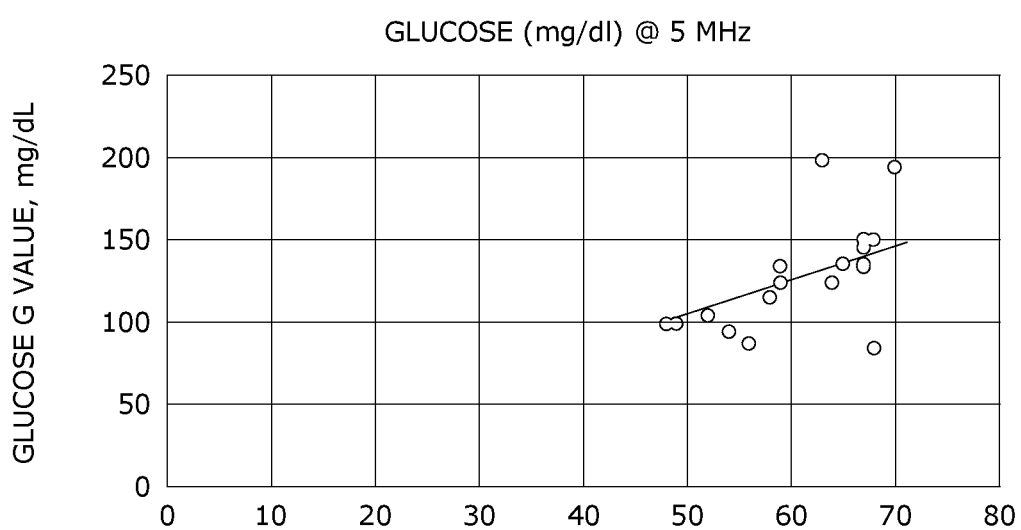
FIG. 6B is a graph of human glucose measured in-vivo by the sensor module of FIG. 2 at 5 MHz.
Figure 6C:
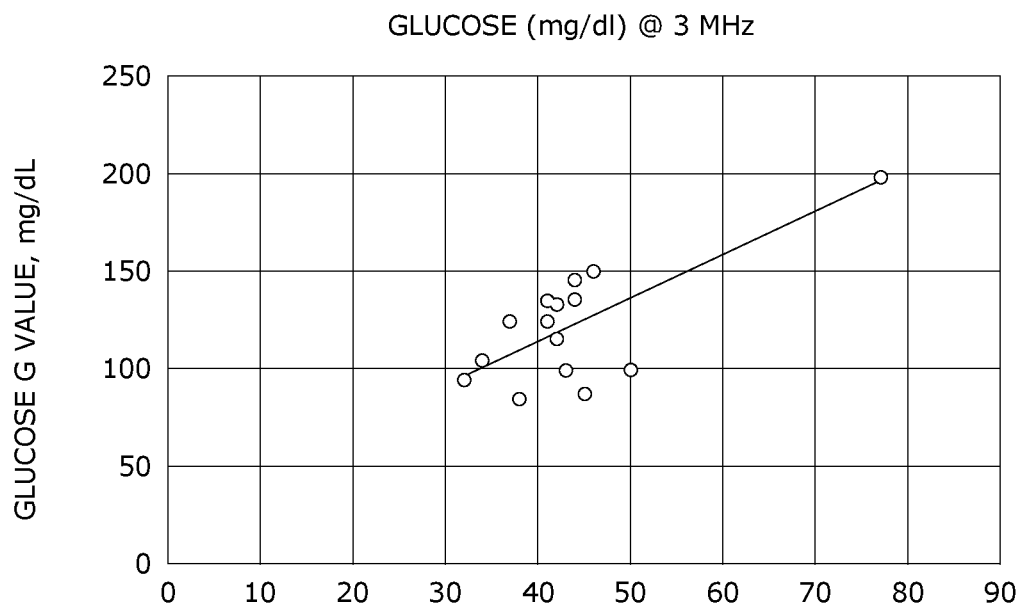
FIG. 6C is a graph of human glucose measured in-vivo by the sensor module of FIG. 2 at 3 MHz.
Figure 6D:
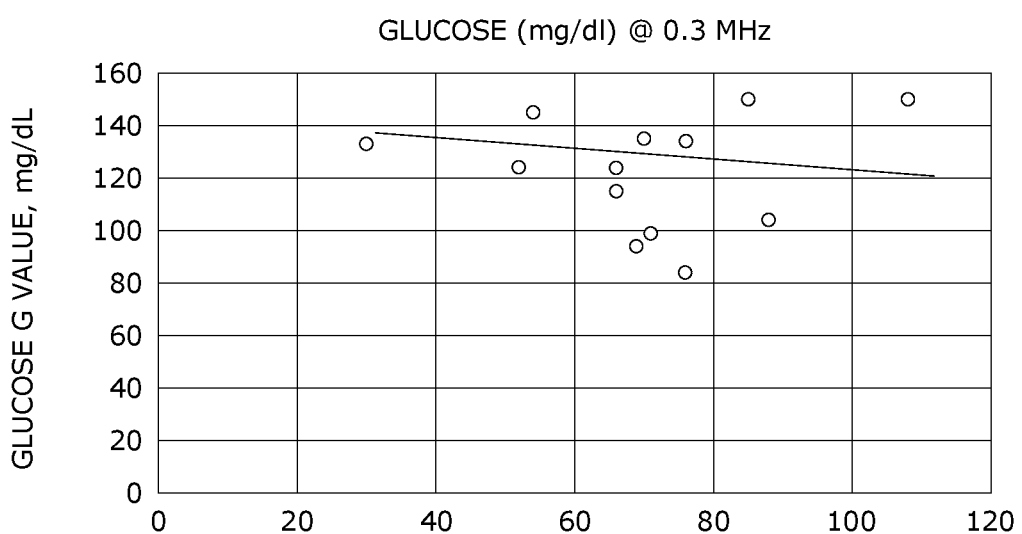
FIG. 6D is a graph of human glucose measured in-vivo by the sensor module of FIG. 2 at 0.3 MHz.

FIGS. 6A through 6D are charts of human glucose data measured in-vivo using a Colpitts sensor module according to an embodiment of the present invention at a series of radiofrequencies: FIG. 6A was measured at 7 MHz; FIG. 6B was measured at 5 MHz; FIG. 6C was measured at 3 MHz; and FIG. 6D was measured at 0.3 MHz, i.e., 320 KHz. The solid lines illustrate estimates of glucose values derived from over 12 separate measurement days and a "memory graph" of glucose readings from a commercial finger pricking system for medical diagnosis of the patient's glucose trends, i.e., they serve as baseline calibration curves from which another patient would determine his/her glucose values by use of this invention.

It should be understood, of course, that the foregoing relates to exemplary embodiments of the invention and that modifications may be made without departing from the spirit and scope of the invention as set forth in the following claims.

What is claimed is:

1. A noninvasive glucose monitoring system operative to measure bioimpedance with magnetic field coils outside a user's finger, comprising:
   a drive-and-sense coil operative to generate a magnetic field in blood in the user's finger to measure blood and glucose electrical conductivity without penetrating the user's finger or drawing blood;
   a finger clip or a coil button, wherein said drive-and-sense coil is contained in said finger clip or said coil button;
   an electronic oscillator with a plurality of circuits comprising radio frequency chokes, said electronic oscillator being in electrical communication with the drive-and-sense coil;
   a microcontroller; and
   a microprocessor; wherein the microcontroller is operative to sequentially select a plurality of radiofrequencies below about $10^7$ Hz at which the magnetic field is generated by the drive-and-sense coil, the electronic oscillator is operative to measure a change in mutual impedance across the drive-and-sense coil for each of the plurality of radiofrequencies, and the microprocessor is operative to calculate a glucose value from the changes in mutual impedance measured by the electronic oscillator.

2. The noninvasive glucose monitoring system of claim 1, further comprising a component selected from the group consisting of a radiofrequency noise reducer, an oscillator stabilizer, and a combination thereof.

3. The noninvasive glucose monitoring system of claim 1, further comprising a component selected from the group consisting of a pulse-oximeter, a thermistor, and a combination thereof.

4. The noninvasive glucose monitoring system of claim 1, further comprising a display.

5. The noninvasive glucose monitoring system of claim 1, further comprising a data storage medium operative to store the glucose value over time.

6. The noninvasive glucose monitoring system of claim 1, further comprising a plurality of capacitors.

7. The noninvasive glucose monitoring system of claim 1, further comprising a battery.

8. A noninvasive method of measuring glucose in-vivo, comprising:
   (a) placing a drive-and-sense coil adjacent to a subject's finger or pressing the subject's finger against a drive-and-sense-coil button;
   (b) generating an electromagnetic field with the drive-and-sense coil at a plurality of frequencies below about $10^7$ Hz, thereby inducing electrical eddy currents in blood in the subject's finger and inducing a secondary magnetic field in the blood in the subject's finger;
   (c) detecting the secondary magnetic field with the drive-and-sense coil by measuring a change in mutual impedance across the drive-and-sense coil for each of the plurality of frequencies; and
   (d) calculating a glucose content in the blood from the change in mutual impedance according to a predetermined correlation.

9. The noninvasive method of measuring glucose in-vivo of claim 8, further comprising measuring a criterion selected from the group consisting of temperature, pulse, oxygen saturation, hematocrit level, and any combination thereof.

10. The noninvasive method of measuring glucose in-vivo of claim 8, further comprising displaying the glucose content on a digital display.

11. The noninvasive method of measuring glucose in-vivo of claim 8, further comprising a step of determining a radiofrequency background value prior to placing the drive-and-sense coil adjacent to the subject's finger or prior to pressing the subject's finger against the drive-and-sense-coil button.

12. The noninvasive method of measuring glucose in-vivo of claim 11, wherein the step of measuring the change in mutual impedance comprises calculating a voltage output difference between the radiofrequency background value and a voltage output attributable to glucose impedance in the subject's finger.

* * * * *